(12) United States Patent
Barten

(10) Patent No.: US 8,492,615 B2
(45) Date of Patent: Jul. 23, 2013

(54) BRASSICA OLERACEA PLANTS WITH A RESISTANCE TO MYCOSPHAERELLA BRASSICICOLA

(75) Inventor: Piet Barten, Aj Noord-Scharwoude (NL)

(73) Assignee: Bejo Zaden B.V., CZ Warmenhuizen (NL)

( * ) Notice: Subject to any disclaimer, the term of this patent is extended or adjusted under 35 U.S.C. 154(b) by 1259 days.

(21) Appl. No.: 12/226,193

(22) PCT Filed: Apr. 12, 2007

(86) PCT No.: PCT/EP2007/053570

§ 371 (c)(1),
(2), (4) Date: Dec. 10, 2008

(87) PCT Pub. No.: WO2007/116096

PCT Pub. Date: Oct. 18, 2007

(65) Prior Publication Data

US 2009/0126036 A1    May 14, 2009

(30) Foreign Application Priority Data

Apr. 12, 2006  (NL) ..................................... 1031584

(51) Int. Cl.
*A01H 5/00* (2006.01)
*A01H 1/00* (2006.01)
*C12N 15/82* (2006.01)

(52) U.S. Cl.
USPC ............................ 800/306; 800/279; 800/266

(58) Field of Classification Search
None
See application file for complete search history.

(56) References Cited

U.S. PATENT DOCUMENTS 7,709,616 B2 *   5/2010   Bentwich et al. ............ 536/23.1

FOREIGN PATENT DOCUMENTS

NL       1 017 616       9/2002

OTHER PUBLICATIONS

Sequence Accession GR283844, Manichaikul et al, May 21, 2010.*
Ende Van den J.E., "A Screening Test for *Mycosphaerella brassicicola* on *Brassica Oleracea*." Netherlands Journal of Plant Pathology, Nederlandse Planteziektenkundige Vereniging, Wageningen, NL, vol. 98, No. 4, 1992, pp. 227-236, XP001031436, ISSN: 0028-2944.
International Preliminary Report on Patentability dated Oct. 14, 2008 in corresponding International Application No. PCT/EP2007/053570.

* cited by examiner

*Primary Examiner* — Elizabeth McElwain
(74) *Attorney, Agent, or Firm* — Harness, Dickey & Pierce, P.L.C.

(57) ABSTRACT

On embodiment of the present invention discloses *Brassica oleracea* plants with a resistance gene to *Mycosphaerella brassicicola*. An embodiment of the invention also discloses a method for providing a *Brassica oleracea* plant with a resistance to *Mycosphaerella brassicicola*, including providing a first *B. oleracea* plant, which plant includes a resistance gene to *M. brassicicola*; crossing the resistant plant with a susceptible second *B. oleracea* plant; isolating from the progeny genomic DNA for detecting the presence of an introgression with the resistance gene using one or more specific DNA markers linked to the resistance gene; and selecting from the progeny a *B. oleracea* plant in which the presence of the introgression with the resistance gene has been demonstrated.

10 Claims, No Drawings

SEQUENCE LISTING

```
<160> NUMBER OF SEQ ID NOS: 5

<210> SEQ ID NO 1
<211> LENGTH: 33
<212> TYPE: DNA
<213> ORGANISM: Artificial
<220> FEATURE:
<223> OTHER INFORMATION: primer 1

<400> SEQUENCE: 1
caggaaacag ctatgacaat gtctctctct ctc                          33

<210> SEQ ID NO 2
<211> LENGTH: 33
<212> TYPE: DNA
<213> ORGANISM: Artificial
<220> FEATURE:
<223> OTHER INFORMATION: primer 2

<400> SEQUENCE: 2
caggaaacag ctatgacttg ctctctctct ctc                          33

<210> SEQ ID NO 3
<211> LENGTH: 33
<212> TYPE: DNA
<213> ORGANISM: Artificial
<220> FEATURE:
<223> OTHER INFORMATION: primer 3

<400> SEQUENCE: 3
caggaaacag ctatgaccac ttctctctct ctc                          33

<210> SEQ ID NO 4
<211> LENGTH: 33
<212> TYPE: DNA
<213> ORGANISM: Artificial
<220> FEATURE:
<223> OTHER INFORMATION: primer 4

<400> SEQUENCE: 4
caggaaacag ctatgacctt ttctctctct ctc                          33

<210> SEQ ID NO 5
<211> LENGTH: 16
<212> TYPE: DNA
<213> ORGANISM: Artificial
<220> FEATURE:
<223> OTHER INFORMATION: primer 5

<400> SEQUENCE: 5
ccaggtgtgt gtgtgt                                             16
```

BRASSICA OLERACEA PLANTS WITH A RESISTANCE TO MYCOSPHAERELLA BRASSICICOLA

The material in the ASCII text file entitled 5100-000073-US_ST25.txt is hereby incorporated by reference in its entirety. The ASCII text file entitled 5100-000073-US_ST25.txt was created 29 Aug. 2011 and the size is 1.13 KB (1,158 bytes).

The present invention relates to *Brassica oleracea* plants which are resistant to *Mycosphaerella brassicicola*, the cause of ringspot disease. The invention also relates to the seeds, fruits and/or other plant parts from these resistant plants. The present invention further relates to a method for providing a *B. oleracea* plant which is resistant to *M. brassicicola*. The invention also relates to the use of specific DNA markers which are specifically linked to the *M. brassicicola* resistance gene for the purpose of identifying resistant *B. oleracea* plants.

*Mycosphaerella brassicicola* (sometimes also appearing under the names *Sphaeria brassicicola, Sphaerella brassicicola, Dothidea brassicae, Asteroma brassicae* and *Phyllosticta brassicicola* (Punithalingham and Holliday, Descriptions of Pathogenic Fungi and Bacteria, CMI (Commonwealth Mycological Institute) England, No. 468, 1975) is the cause of the so-called ringspot disease in *Brassica* plants. The fungus, which has occurred in many places since the beginning of the eighties and in some cases has even reached epidemic proportions, belongs to the Ascomycetes and forms grey-brown lesions on the leaves of the plants, in which eventually the ascospores are formed. These spores are the means of dissemination of the fungus and are spread mainly by wind and rain drops. The fungus thrives best in moist and temperate conditions. Due to a combination of factors *M. brassicicola* can spread rapidly over a large area. A serious infection with *M. brassicicola* can result in rapid leaf ageing, defoliation and consequent reduced crop yield. In addition, this can lead to cosmetic damage to the product (the plant and/or parts of the plant), also because the *M. brassicicola* infection may even spread during storage of the product, and because the lesions form an invasion site for secondary infections (for instance *Botrytis* spp.).

The host plants of *M. brassicicola* comprise nearly all *Brassica* species, including *B. campestris, B. carinata, B. napus, B. nigra, B. oleracea*, and further *Raphanus sativus*, and also some cruciferous weeds, including *Hirschfeldia incana, Matthiola incana, Sisymbrium officinale*, and *Thlaspi arvense*.

*Brassica* is a plant genus in the family Brassicaceae (formerly Cruciferae). The members of this genus are collectively referred to as cabbage or mustard. The genus *Brassica* comprises a number of important agricultural and horticultural crops, including rape, cauliflower, red cabbage, savoy cabbage, white cabbage, oxheart cabbage, curly cale cabbage, broccoli, Brussels sprouts, Chinese cabbage, turnip cabbage and Portuguese cabbage (tronchuda). Almost all parts of the plants are used as food, such as the roots (turnip), stalks (turnip cabbage), leaves (white cabbage), axillary buds (sprouts), flowers (cauliflower, broccoli) and seeds (rape). Some species with white or purple flowers or distinct colour or shape of the leaves are cultivated for ornamental purposes.

Although control of *M. brassicicola* is possible using fungicides, the number of permitted agents and the use of these agents is becoming increasingly limited for environmental and health-related reasons. Using fungicides to control *M. brassicicola* is moreover not easy because the correct moment for treatment is difficult to determine. It is therefore desirable for *Brassica* plants, in particular *Brassica oleracea* plants, to be developed which are resistant to the above described fungus. There are no *Brassica* varieties available with a resistance to *M. brassicicola*.

The object of the present invention is to provide a *Brassica oleracea* plant with a resistance to *M. brassicicola*, the cause of ringspot disease.

The invention provides to this end a *Brassica oleracea* plant comprising a resistance gene to *M. brassicicola*, wherein said resistance gene provides a monogenic and dominant resistance to *M. brassicicola*, and wherein the resistance gene is derived from the *B. oleracea* plant, the seeds of which have been deposited in the American Type Culture Collection (ATCC, Patent Depository, 10801 University Boulevard, Manassas, Va. 20110, United States of America) on 1 Mar. 2006 under number PTA-7413. Surprisingly, it has been found that with the resistance gene according to the invention a dominant resistance is provided to two physiological species (physio's) of *M. brassicicola*. These are a physiological species frequently occurring in the Netherlands and a more virulent physiological species frequently encountered in the cauliflower regions in Western France (particularly Normandy and Brittany) and in cabbage regions in Central America (particularly Guatemala).

In a further preferred embodiment of the invention, the resistance gene in the *B. oleracea* plant is linked to one or more specific DNA markers. These markers can be used to demonstrate the presence of the resistance gene of the invention.

In a preferred embodiment of the invention the resistance gene to *M. brassicicola* is linked to at least two, preferably at least three, more preferably at least four, more preferably at least five, most preferably six DNA markers, wherein the DNA markers enclose the resistance gene. "Enclose" in the present application is understood to mean that the DNA markers are located on the genome on both sides of the resistance gene, i.e. "upstream" as well as "downstream" of the resistance gene. Demonstrating the presence of a plurality of DNA markers, which are linked to the resistance gene, and enclose the resistance gene ensure that the introgression with the resistance gene is actually present.

The DNA markers according to the invention are preferably selected from table 1, wherein the presence of the DNA markers in the genome of the plant is demonstrated using the primer sequences selected from the group consisting of SEQ ID NO: 1 up to and including SEQ ID NO: 5.

In the research which has led to the present invention it has been demonstrated that the relevant DNA markers are characteristic for the introgression of the resistance to *M. brassicicola*. The DNA markers according to the invention are DNA fragments which are linked to the relevant resistance gene, have a determined size (bp) as indicated in table 1, and can be demonstrated by using specific primer combinations.

The plant according to the invention is preferably selected from the group consisting of *B. oleracea* convar. *botrvtis* var. *botrvtis* (cauliflower, romanesco), *B. oleracea* convar. *botrvtis* var. *cymosa* (broccoli), *B. oleracea* convar. *botrvtis* var. *asparagoides* (sprouting broccoli), *B. oleracea* convar. *oleracea* var. *gemnifera* (Brussels sprouts), *B. oleracea* convar. *capitata* var. *alba* (white cabbage, oxheart cabbage), *B. oleracea* convar. *capitata* var. *rubra* (red cabbage), *B. oleracea* convar. *capitata* var. *sabauda* (savoy cabbage), *B. oleracea* convar. *acephela* var. *sabellica* (curly cale cabbage), *B. oleracea* convar. *acephela* var. *gongyloides* (turnip cabbage) and *B. oleracea* var. *tronchuda* syn. *costata* (Portuguese cabbage). The invention also relates to the seeds, fruits and/or other plant parts from the above described plants. Plant parts are here understood to mean, among others, the edible parts of the plant, such as for instance axillary buds (sprouts).

The invention also relates to a method for obtaining a *B. oleracea* plant with a resistance to *M. brassicicola*, which method comprises at least the following steps of:

(a) providing a first *B. oleracea* plant, which plant comprises a resistance gene to *M. brassicicola;*

(b) crossing the resistant plant with a susceptible second *B. oleracea* plant;

(c) isolating from the progeny genomic DNA for detecting the presence of an introgression with the resistance gene using one or more specific DNA markers linked to the resistance gene; and (d) selecting from the progeny a *B. oleracea* plant in which the presence of the introgression with the resistance gene has been demonstrated in step (c).

With the method according to the invention resistant *B. oleracea* plants can be provided in a rapid and simple manner by making use of DNA markers which are specific to the introgression with the resistance gene according to the invention.

The disease pressure of *M. brassicicola* can be very variable due to different natural factors such as wind, temperature, air humidity and environment (inter alia other host plants). Great differences in the degree of infection can hereby occur. Furthermore, the symptoms can easily be confused with the diseases caused by *Alternaria brassicae* and *A. brassicicola*. Using the method according to the present invention and the use of the specific DNA markers linked to a resistance gene it is possible to determine in simple manner whether a plant contains the resistance gene. In this manner resistant *B. oleracea* plants can moreover be obtained more quickly than with the conventional breeding programs. Many *Brassica* species have a biannual cycle in which the plant is vegetative in the first year and flowers and produces seed in the second year. By utilizing the specific DNA markers linked to a resistance gene the process can be accelerated to an annual cycle because it is not necessary to perform a disease test and nor do the plants have to be grown to an adult stage to make selection possible. Many years can thus be saved in the overall breeding program.

The plants selected in step (d) of the method according to the invention can optionally be subjected to additional steps, such as back-crossing or self-pollination the plant obtained in step (d) one or more times with a susceptible *B. oleracea* plant and subsequently selecting once again from the progeny a resistant *B. oleracea* plant using the specific DNA markers. The plants obtained in step (d) can for instance also be made homozygous by means of techniques known to the skilled person such as anther and/or microspore culture.

The first *B. oleracea* plant preferably comprises a resistance gene which gives a monogenic and dominant resistance to *M. brassicicola*.

In a preferred embodiment the first *B. oleracea* plant comprises a resistance gene derived from the *B. oleracea* plant, the seeds of which have been deposited in the American Type Culture Collection (ATCC, Patent Depository, 10801 University Boulevard, Manassas, Va. 20110, United States of America) on 1 Mar. 2006 under number PTA-7413.

In a further preferred embodiment of the method according to the invention the selection of the resistant *B. oleracea* plant in step (d) comprises of selecting a *B. oleracea* plant which comprises at least two, preferably at least three, more preferably at least four, more preferably at least five and most preferably six DNA markers linked to the resistance gene, wherein the DNA markers enclose the resistance gene. It is hereby possible to determine with certainty that the plant actually possesses the introgression with the resistance gene.

The DNA markers according to the invention are preferably selected from table 1, wherein the presence of the DNA markers in the genome of the plant is demonstrated using the primer sequences chosen from the group consisting of SEQ ID NO: 1 up to and including SEQ ID NO: 5 (table 2).

In a particular embodiment according to the invention the first *B. oleracea* plant comprises a resistance gene to *M. brassicicola* originating from a *B. oleracea* plant, the seeds of which have been deposited in the American Type Culture Collection (ATCC, Patent Depository, 10801 University Boulevard, Manassas, Va. 20110, United States of America) on 1 Mar. 2006 under number PTA-7413.

The susceptible *B. oleracea* plant into which the resistance gene is inserted is preferably selected from the group consisting of *B. oleracea* convar. *botrytis* var. *botrytis* (cauliflower, romanesco), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemnifera* (Brussels sprouts), *B. oleracea* convar. *capitata* var. *alba* (white cabbage, oxheart cabbage), *B. oleracea* convar. *capitata* var. *rubra* (red cabbage), *B. oleracea* convar. *capitata* var. *sabauda* (savoy cabbage), *B. oleracea* convar. *acephela* var. *sabellica* (curly cale cabbage), *B. oleracea* convar. *acephela* var. *gongyloides* (turnip cabbage) and *B. oleracea* var. *tronchuda* syn. *costata* (Portuguese cabbage).

The invention further relates to *B. oleracea* plants obtainable by the above described method, and to the seeds and/or plant parts thereof.

The invention also relates to the use of at least one DNA marker linked to a resistance gene to *M. brassicicola*, for identifying a *B. oleracea* plant which is resistant to *M. brassicicola*, wherein the DNA marker is selected from the DNA markers of table 1 and wherein the DNA marker is demonstrated with the primer sequences selected from the group consisting of SEQ ID No.: 1-5 (table 2).

The resistance gene preferably originates from the *B. oleracea* plant of which the seeds have been deposited in the American Type Culture Collection (ATCC) under number PTA-7413.

The invention is further elucidated on the basis of the following example.

EXAMPLE

The *M. brassicicola*-resistant parent line *B. oleracea* (9009899, cauliflower-type; deposited at ATCC under number PTA-7413) was crossed with different *B. oleracea* species (turnip cabbage, broccoli, oxheart cabbage, white cabbage, red cabbage, curly cale cabbage, savoy cabbage, tronchuda, Brussels sprouts and cauliflower). BC1 populations were obtained after backcrossing with the susceptible parent lines.

Field tests were performed in different years. Plant material was collected in a year in which the degree of infection by *M. brassicicola* was high and occurred uniformly in the different *Brassica* species. The development of DNA markers for the resistance to *M. brassicicola* was started with these populations. The populations almost all had a 1:1 split in respect of the *M. brassicicola* resistance, which indicates the expected monogenic dominant resistance.

Three populations (oxheart cabbage, broccoli and turnip cabbage) were used, each of about 150 individuals. DNA of all individuals was isolated from leaf punches (~0.3 cm$^2$/leaf punch). A BSA (bulked segregant analysis) method was subsequently used to generate closely linked DNA markers, wherein use was made of the RAMP technique (Matsumoto et al., Mammalian Genome, 9: 531-535, 1998; Reiter, PCR-based marker systems, in: DNA-based markers in plants, Kluwer Academic Publishers, vol. 6: 9-29, 2001; Weising et al., Detecting DNA variation by molecular markers, in: DNA fingerprinting in plants, principles, methods and applications, CRC Press, 2nd ed.: 21-73, 2005).

The RAMP technieque, wherein an iSSR and a RAPD-primer are combined, produces band patterns having DNA fragments therein which specifically co-segregate with the resistance, whereby a distinction can be made between individuals which do contain the resistance gene-introgression and individuals which do not contain the introgression. Exemplary RAPD-primers include Operon RAPD® 10-mer kits A-01 to Z-20 (Operon Biotechnologies, Inc. Huntsville, USA).

By mapping the RAMP-fragments, closely linked RAMP-markers were identified which fall within the introgression and enclose the resistance gene, see table 1. The genetic distance between the DNA marker and the resistance gene is shown in centimorgans (cM).

Marker Analysis and PCR Conditions

The general PCR conditions in which the DNA markers were generated are shown in the summary below.

PCR Mix for RAMP Reaction:

Per Reaction about 1 ng genomic plant DNA 75 mM Tris-HCL (pH 8.8)

20 mM $NH_4SO_4$ 0.01% (v/v) Tween 20

2.8 mM $MgCl_2$ 0.15 µM forward primer 0.20 µM reverse primer 0.25 mM dNTP 0.04 units/µl Red Hot® DNA polymerase (Abgene, Epsom, UK)

| PCR program: | | |
|---|---|---|
| | RAPD35 | Number of cycles |
| 1 | 2 min. 93° C. | 1 |
| 2 | 30 sec. 93° C. | |
| 3 | 30 sec. 35° C. | |
| 4 | heating by 0.3°/sec to 72° C. | |
| 5 | 1 min. 30 sec 72° C. | |
| 2-5 | | 40 |
| 6 | 5 min 72° C. | 1 |

PAGE/Licor

For analysis of the RAMP patterns use was made of a "GeneReadIR 4200 DNA analyzer" (Licor Inc.). On the basis of an optimal concentration of 6.5% acryl amide, fragments can be separated down to a single base. In order to make the fragments visible on this system it is necessary to use labelled (IRDye labels) primers. For this purpose a third of the quantity of forward primer was replaced by a labelled primer with the same sequence.

Marker Overview

In the research which has led to the present invention the primers referred to in table 2 have been used to generate the DNA markers referred to in table 1.

TABLE 1

Overview of RAMP markers

| RAMP SEQ ID Combination | Fragment size (bp) | Position in cM relative to resistance gene |
|---|---|---|
| 1 + RAPD® 10-mer | 198 | 2.4 |
| 2 + RAPD® 10-mer | 360 | 0.7 |
| 3 + RAPD® 10-mer | 370 | 0.3 |
| 4 + RAPD® 10-mer | 230 | 1.2 |
| 5 + RAPD® 10-mer | 173 | 2.1 |
| 5 + RAPD® 10-mer | 473 | 3.2 |

TABLE 2

Overview of SEQ ID nos

| SEQ ID no. | Sequence |
|---|---|
| 1 | iSSR CAGGAAACAGCTATGACAATGTCTCTCTCTC |
| 2 | iSSR CAGGAAACAGCTATGACTTGCTCTCTCTCTC |
| 3 | iSSR CAGCAAACAGCTATGACCACTTCTCTCTCTC |
| 4 | iSSR CAGGAAACAGCTATGACCTTTTCTCTCTCTC |
| 5 | iSSR CCAGGTGTGTGTGTGT |

The primer combinations form fragments with a specific size on the resistance gene introgression (Table 1). These DNA markers are therefore characteristic for the resistance gene introgression. The combination of these DNA markers enclosing the resistance gene provides conclusive evidence that the *M. brassicicola* resistance gene introgression is present.

Definitions

BSA—Bulked Segregant Analysis—selection strategy wherein, in large segregating populations, individuals with the same trait (phenotype) or DNA of these individuals are bulked into "pools". After screening of these pools with DNA techniques, markers are identified which are linked to the relevant phenotype.

cM—centimorgan—unit for the genetic distance between markers, based on the number of crossing-overs per hundred individuals.

DNA marker—a DNA fragment which is linked to a gene or another piece of DNA with a known location on the genome, which is used to monitor heritability of this gene or this location.

Gel-electrophoresis—method for separating molecules (DNA, RNA, protein among others) on the basis of their size, shape or charge, in a matrix (agarose or polyacrylamide) under the influence of an electrical field.

Introgression—a chromosome fragment of a line which can for instance be inserted into another line by crossing.

IRDye labels—infrared labels which are used for Licor imaging systems, the detection of which takes place at 700 nm or 800 nm.

Monogenic—determined by one gene

PCR—Polymerase Chain Reaction—an in vitro amplification method for multiplying a specific DNA fragment. This synthesis reaction makes use of a minimum of one oligonucleotide which hybridizes with a piece of DNA, whereafter a polymerase amplifies the flanking region during successive temperature cycles.

Primer—a short oligonucleotide (~20-50 bp) complementary to the sequence of a single-strand DNA molecule, which serves as starting point of a polymerase.

RAMPs—Random Amplified Microsatellite Polymorphisms—DNA fingerprinting technique based on RAPD and iSSR primers with which polymorphisms between different DNA monsters are detected.

RAPD—Random Amplified Polymorphic DNA—Random Amplified Polymorphic DNA primer: A 10-mer with a "random" sequence, wherein the GC-content lies between 60% and 70% and wherein the primer ends are not self-complementary.

iSSR—inter Simple Sequence Repeat—Inter Simple Sequence Repeat primer: A primer designed on the 5' end of an SSR (Single Sequence Repeat); a piece of DNA consisting of a repetition of 2 or 3 nucleotides BC—Backcrossing—crossing of an individual with one of the original parents.

The invention claimed is:

1. *Brassica oleracea* plant, comprising a resistance gene to *Mycosphaerella brassicicola*, wherein the resistance gene is derived from a *B. oleracea* plant, the seeds of which have been deposited at the American Type Culture Collection (ATCC) under number PTA-7413.

2. Plant as claimed in claim 1, wherein the resistance gene to *M. brassicicola* is linked to at least one specific DNA marker.

3. Plant as claimed in claim 2, wherein the resistance gene to *M. brassicicola* is linked to at least two DNA markers, wherein the at least two DNA markers enclose the resistance gene.

4. Plant as claimed in claim 3, wherein the resistance gene to *M. brassicicola* is linked to at least three DNA markers, wherein the at least three DNA markers enclose the resistance gene.

5. Plant as claimed in claim 4, wherein the resistance gene to *M. brassicicola* is linked to at least four DNA markers, wherein the at least four DNA markers enclose the resistance gene.

6. Plant as claimed in claim 5, wherein the resistance gene to *M. brassicicola* is linked to at least five DNA markers, wherein the at least five DNA markers enclose the resistance gene.

7. Plant as claimed in claim 6, wherein the Resistance gene to *M. brassicicola* is linked to at least six DNA markers, wherein the at least six DNA markers enclose the resistance gene.

8. Plant as claimed in claim 2, wherein the at least one DNA marker is selected from table 1, and wherein the presence of the at least one DNA marker in the genome of the plant is demonstrated with a primer sequence selected from the group consisting of SEQ ID NO:1 to SEQ ID NO:5, each sequence being in combination with a RAPD primer.

9. Plant as claimed in claim 1, wherein the plant is selected from the group consisting of *Brassica oleracea* convar. *botrytis* var. *botrytis*, *Brassica oleracea* convar. *botrytis* var. *cymosa* (broccoli), *Brassica oleracea* convar. *botrytis* var. *asparagoides*, *Brassica oleracea* convar. *oleracea* var. *gemnifera*, *Brassica oleracea* convar. *capitata* var. *alba*, *Brassica oleracea* convar. *capitata* var. *rubra*, *Brassica oleracea* convar. *capitata* var. *sabauda*, *Brassica oleracea* convar. *acephela* var. *sabellica*, *Brassica oleracea* convar. *acephela* var. *gongyloides* and *Brassica oleracea* var. *tronchuda* syn. *costata*.

10. Seeds, fruits and/or other plant parts from a plant as claimed in claim 1.

* * * * *